(12) United States Patent
Hull et al.

(10) Patent No.: US 9,612,190 B2
(45) Date of Patent: Apr. 4, 2017

(54) BOND EVALUATION USING PIEZOCHROMIC FLUORESCENCE

(71) Applicant: The Boeing Company, Chicago, IL (US)

(72) Inventors: John R. Hull, Sammamish, WA (US); Keith J. Davis, Seattle, WA (US); Richard H. Bossi, Renton, WA (US)

(73) Assignee: The Boeing Company, Chicago, IL (US)

( * ) Notice: Subject to any disclaimer, the term of this patent is extended or adjusted under 35 U.S.C. 154(b) by 919 days.

(21) Appl. No.: 13/748,278

(22) Filed: Jan. 23, 2013

(65) Prior Publication Data

US 2014/0202239 A1    Jul. 24, 2014

(51) Int. Cl.
| | | |
|---|---|---|
| *G01N 19/04* | (2006.01) | |
| *G01N 19/00* | (2006.01) | |
| *G01N 21/62* | (2006.01) | |
| *G01N 21/00* | (2006.01) | |
| *G01L 1/24* | (2006.01) | |

(52) U.S. Cl.
CPC ............ *G01N 19/04* (2013.01); *G01L 1/24* (2013.01); *G01N 19/00* (2013.01); *G01N 21/00* (2013.01); *G01N 21/62* (2013.01)

(58) Field of Classification Search
CPC ........ G01N 19/04; G01N 21/00; G01N 21/25; G01N 21/62; G01L 1/24
USPC ...................................................... 73/150 A
See application file for complete search history.

(56) References Cited

U.S. PATENT DOCUMENTS

| | | | | |
|---|---|---|---|---|
| 5,490,426 A | * | 2/1996 | Shiga | G01L 5/0047 73/762 |
| 5,817,945 A | * | 10/1998 | Morris | G01L 11/02 73/762 |
| 6,072,568 A | * | 6/2000 | Paton | G01L 1/24 356/32 |
| 6,157,038 A | * | 12/2000 | Swain | G03G 15/751 250/302 |
| 6,219,139 B1 | * | 4/2001 | Lesniak | G01L 1/241 356/34 |

(Continued)

FOREIGN PATENT DOCUMENTS

| | | | |
|---|---|---|---|
| JP | 2006038586 A | * | 2/2006 |
| WO | 0111311 A1 | | 2/2001 |

OTHER PUBLICATIONS

Jorda, Erie H. et al., Bond Strength and Stress Measurements in Thermal Barrier Coatings, American Society of Mechanical Engineers, Dec. 1, 1997.*

(Continued)

*Primary Examiner* — Hezron E Williams
*Assistant Examiner* — Marrit Eyassu
(74) *Attorney, Agent, or Firm* — Felix L. Fischer (57) ABSTRACT

A composite bonded structure with integral stress sensing and bond evaluation system incorporates a bonded structure having a first component, a second component and a layer of adhesive bonding the first and second components. The layer of adhesive includes multiple embedded fluorescing particles which emit a first spectral intensity in an unstressed condition and a second spectral intensity in a stressed condition. A bond evaluation apparatus is then employed for measuring spectral intensity.

19 Claims, 7 Drawing Sheets

(56) References Cited

U.S. PATENT DOCUMENTS

| | | | |
|---|---|---|---|
| 6,943,869 B2* | 9/2005 | Hubner | G01L 1/241 |
| | | | 356/34 |
| 2004/0155927 A1* | 8/2004 | Nakao | B41J 2/14 |
| | | | 347/54 |
| 2005/0102871 A1 | 5/2005 | Merle | |
| 2005/0115331 A1 | 6/2005 | Fonov | |
| 2006/0159513 A1* | 7/2006 | Breuer | F16B 11/006 |
| | | | 403/27 |
| 2007/0026532 A1* | 2/2007 | Ikami | B01L 3/5085 |
| | | | 436/172 |
| 2012/0094397 A1* | 4/2012 | Horii | G01N 33/557 |
| | | | 436/518 |

OTHER PUBLICATIONS

Choi, C. L., Kolki, K. J., Olson, A. C. K. and Alivisatos, A. P., "Luminescent nanocrystal stress gauge," Proc. Nat. Acad. Sci, vol. 107, 21306-21310. (2010).

Zhang, G.; Lu, J.; Sabat, M. and Fraser, C. L., Polymorphism and reversible mechanochromic luminescence for solid-state difluoroboron avobenzone, J. Am. Chem. Soc., vol. 132, pp. 2160-2162 (2010).

Rodriguez-Lazcano, Y., Nataf, L. and Rodriguez, F., "Electronic structure and luminescence of [(CH3)4N]2MnX4 (X=Cl,Br) crystals at high pressures by time-resolved spectroscopy: Pressure effects on the Mn—Mn exchange coupling," Phys. Rev. B vol. 80, 085115 (2009).

* cited by examiner

BOND EVALUATION USING PIEZOCHROMIC FLUORESCENCE

BACKGROUND INFORMATION

Field

Embodiments of the disclosure relate generally to the field of bond stress measurement and more particularly to a method for use of piezochromic fluorescing materials embedded within a composite bond line illuminated with light, having a wavelength less than the fluorescent wavelength allowing measurement of a wavelength at which the maximum intensity occurs and a wavelength shift at the maximum intensity for determination of average stress on the bond.

Background

Composite materials are used in many structural applications throughout the aerospace and automotive industries. Many present and expected future products for commercial aircraft make extensive use of composite materials. Present practice connects composite components with fasteners of different types. It would be an improvement in simplicity of design, costs could be lowered, and improved protection against lightning strikes obtained by bonding different composite components together using adhesive. However, inspection techniques for evaluation of the health of such bonds in a nondestructive manner are not available.

It is therefore desirable to provide a method for evaluating bonds between layers of composite materials which is efficient, effective and can be accomplished in a non-destructive manner.

SUMMARY

Embodiments disclosed herein provide a composite bonded structure with integral stress sensing and bond evaluation system which incorporates a bonded structure having a first component, a second component and a layer of adhesive bonding the first and second components. The layer of adhesive includes multiple embedded fluorescing particles which emit a first spectral intensity in an unstressed condition and a second spectral intensity in a stressed condition. A bond evaluation apparatus is then employed for measuring spectral intensity.

The embodiments allow a process for bond stress measurement in which fluorescing particles sensitive to stress are identified and mixed within adhesives subsequently used in a bond between two layers of material. A stimulus light of appropriate wavelength is provided and the fluorescent light emitted from the fluorescing particles is observed. The emitted light is indicative of the stress experienced by the fluorescing particles. The fluorescent light characteristics may then be translated into stress data.

The features, functions, and advantages that have been discussed can be achieved independently in various embodiments of the present disclosure or may be combined in yet other embodiments further details of which can be seen with reference to the following description and drawings.

DETAILED DESCRIPTION

Embodiments disclosed herein provide a method for evaluation of the state of adhesive bonds such as might be formed between two panels of composite material and in particular to determine the degree of stress on the adhesive at different spatial locations within the bond. A number of small piezochromic fluorescent particles are placed in the adhesive. The size and number of the particles are sufficiently small that they do not impact the strength of the bond. Light, with a wavelength less than the fluorescent wavelength of the particles, illuminates a portion of the bond. Over this given portion of the bond, or a part thereof (the measurement zone), the spectral intensity of the fluorescent light is measured. The wavelength at which the maximum intensity occurs with no stress on the bond is then determined. A wavelength shift at the maximum intensity may then be measured that is proportional to the average stress on the portion of the bond in the measurement zone. For material compositions in which the material and the bond are sufficiently transparent to the light required for inducing the fluorescence and the resulting fluorescent signal, the light can be shown directly on the bond and the emitted light directly measured. For materials that are not sufficiently transparent, e.g., carbon-fiber composites, one or more light transmitting pathways are introduced into the structure. An example of such a pathway is an optically transparent glass fiber. Such glass fibers take up a small fraction of the composite or the bond and do not significantly impact the strength of either.

Figure 1:
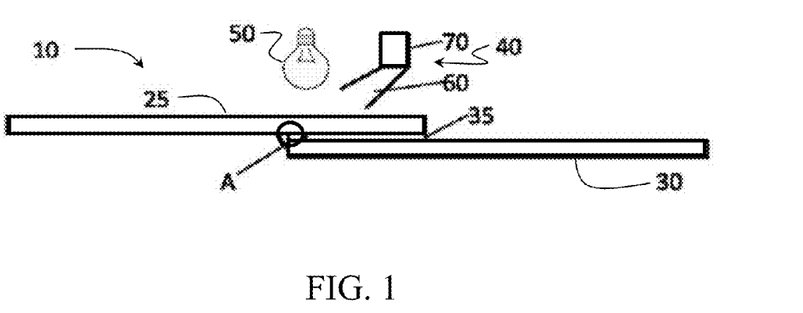
FIG. 1 is a side section view of a lap bond in a composite bonded structure with integral stress sensing employing a first embodiment and a bond evaluation system.

Referring to the drawings, FIG. 1 shows a composite bonded structure with integral stress sensing 10 incorporating an upper fiber composite component 25, a lower fiber-composite component 30 and an adhesive layer 35 between the two composite components bonding the composite components over at least a portion of their length. The adhesive layer 35, shown in detail in FIG. 2, includes a matrix of adhesive 80, in which a collection of fluorescing particles 90, to be described in greater detail subsequently, are dispersed in approximately a homogeneous manner. For the embodiment shown in the side section view of FIG. 1, a lap bond is used in the composite structure. Alternative embodiments to those specifically described herein and incorporated in the stress detection method described may include butt joints, layered skins, scarf joints, mortise joints or other joints employed in adhesive bonding.

Returning to FIG. 1, a bond evaluation apparatus 40 employs a light source 50, a light detector 60, and a spectrum analyzer 70. The light source 50 can be a lamp as shown in the drawings or, preferably, a laser shining light at a discrete wavelength. The discrete wavelength provided by a laser aids in minimizing the distribution of the spectral intensity and also facilitates interrogating the bond over smaller areas. Spectrum analyzer 70 may be selected from a broad class of instruments capable of measuring light intensity at different wavelengths that include multi-spectral imagers with tunable filters, systems of CCD sensors with lenses and comparable systems.

The light source 50 emits photons that impinge on the upper composite layer 25, a fraction of which penetrates layer 25. Some of the photons in this penetrative fraction are absorbed in adhesive layer 35 by the fluorescing particles 90. Fluorescing particles 90 then fluoresce at a frequency that is lower than that of the incident light. A fraction of the fluoresced light penetrates through layer 25 and is detected by light detector 60. Spectrum analyzer 70 determines the wavelength of the photons collected by detector 60 and reports the spectral intensity. A determination of the spectral intensity with no stresses on the bond 35 or alternatively spectral intensity of the fluorescing particles in solution or otherwise in an unstressed condition provides a baseline condition. Load imposed on the composite bonded structure 10 or deformation within the structure due to damage or other internal stresses creates a change of stress in the bond 35. A determination of the spectral intensity of the fluoresced light in the stressed condition demonstrates a shift from the baseline spectral intensity which is proportional to the stress in the bond. Generalized stress over the entire bond may be measured or localized stresses determined based on scanning of the bond by the detector 60 using structural components similar to ultrasonic non-destructive inspection (NDI) scanning systems for carriage of the detector such as that disclosed in U.S. patent application Ser. No. 13/601,612 filed on Aug. 31, 2012 entitled ULTRASONIC ARRAY TRANSDUCER HOLDER AND GUIDE FOR FLANGES HAVING CUTOUTS AND ASYMMETRIC GEOMETRY having a common assignee as the present application.

Figure 2:
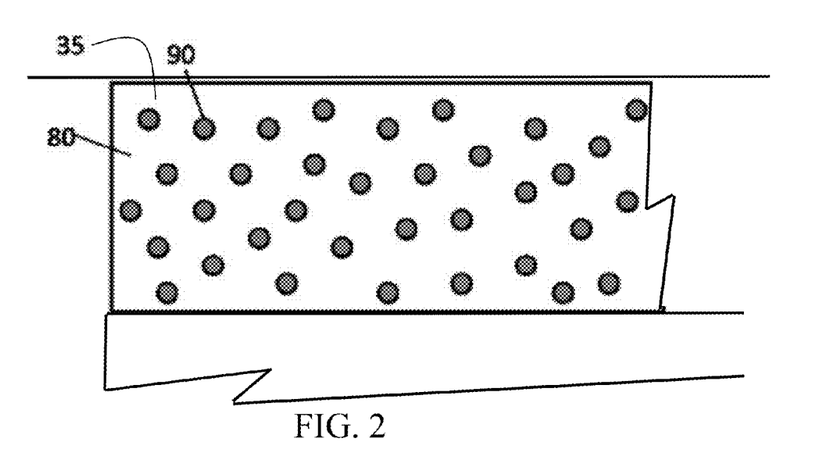
FIG. 2 is a detailed section view of the bond layer in FIG. 1.

The fluorescing particles 90 employed in the bond may be quantum dots or similar structures created using cadmium selenide (CdSe) or alternative fluorescing materials such as alpha-alumina, difluoroboron complex $BF_2AVB$ synthesized from Avobenzone (AVB) via $BF_3$, diphenylflavolene, $CuMoO_4 \cdot OEt2$ boronation in $CH_2Cl_2$ or crystals of $[(CH_3)_4N]_2MnCl_4$ and $[(CH_3)_4N]_2MnBr_4$.

In alternative embodiments, as opposed to introducing the quantum dots or other fluorescing particles directly into the adhesive layer, quantum dots may be dispersed in a transparent fiber having a small diameter of approximately 1 to 50 microns, and the fiber chopped up into small lengths of approximately 25 to 1000 microns and inserted into the adhesive. The advantage of this embodiment is that the quantum dots are better protected from chemical deterioration. A further advantage is that the piezochromic performance of the quantum dots can be readily calibrated by stressing the fiber and measuring the fluorescence before the fiber is chopped into small lengths to establish the baseline fluorescing condition.

Figure 3:
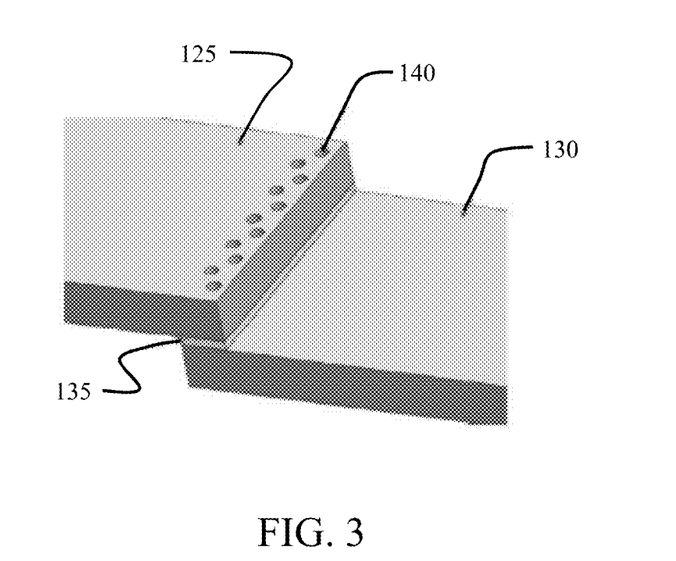
FIG. 3 is an isometric representation of a second embodiment of a composite bonded structure with integral stress sensing.

If upper composite layer 25 is opaque to either the incident or the fluorescent light, alternate embodiments for the composite bonded structure with integral stress sensing, such as that shown in FIG. 3, may be employed. Upper composite layer 125 has a series of holes 140 passing through the thickness of layer 125 in the vicinity of the adhesive bond layer 135. The holes can be regularly or irregularly spaced. The holes 140 can be left open or filled with a transparent polymer, such as acrylic, polycarbonate, clear epoxy, polyurethane, acetate, polystyrene, etc. The holes must have a sufficiently large diameter that light can pass through the holes without significant absorption by the composite layer 125 surrounding the holes. In exemplary applications a diameter of 10 microns or larger for visible wavelengths is employed If the diameter of the holes is large relative to the structural size of the components, the composite may be weakened. However, filling of the holes or limiting the diameters may avoid any detrimental structural effects.

Figure 4:
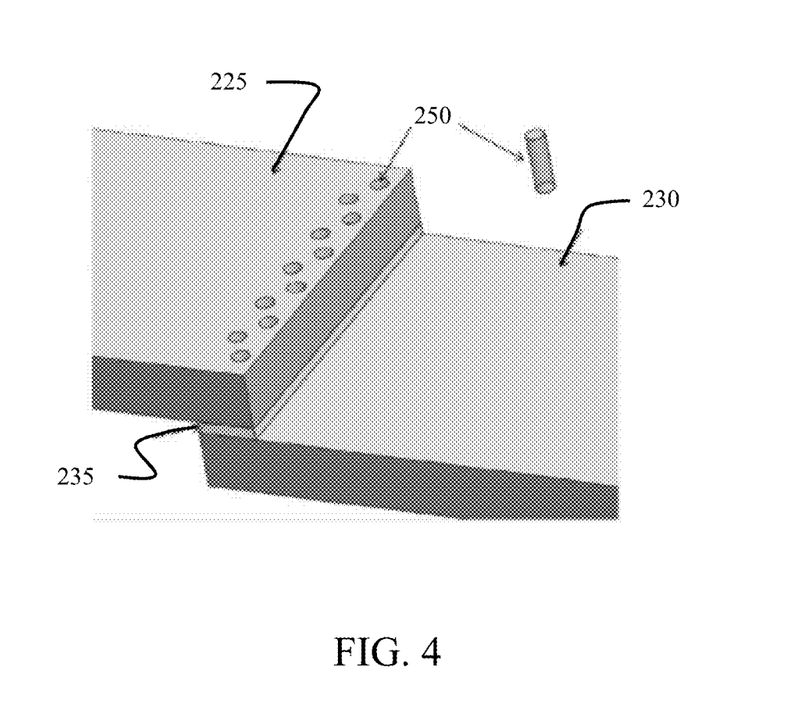
FIG. 4 is an isometric representation of a third embodiment of a composite bonded structure with integral stress sensing.

An alternate embodiment, shown in FIG. 4, can be used to avoid structural issues created by open holes. In this embodiment, the holes 140 are filled with glass fibers 250 in upper fiber composite component 225. The glass fiber 250 can be relatively small in diameter (example embodiments employ fibers of approximately 1 to 50 microns in diameter and fibers are shown with exaggerated size in the figures for clarity) and can be inserted into the upper composite layer 225 before the composite cures. Most of the light incident on the upper flat edge of the fiber light source 50 of the of the bond evaluation system 40 as described with respect to FIG. 1 will easily enter the fiber. As the light travels down the fiber, it is likely to experience total internal reflection when it is incident on the fiber perimeter, so that most of the light entering the glass fiber will make it into the adhesive layer 235 bonding upper fiber composite component 225 to lower fiber composite component 230. In practice the fiber can be of dimensions equivalent to a single-mode optical fiber or a conventional glass fiber used in fiber-glass composites. Such a fiber might have a diameter of 10 microns. A fiber of diameter this small will have a negligible effect on the strength of the composite panel 225.

Figure 5:
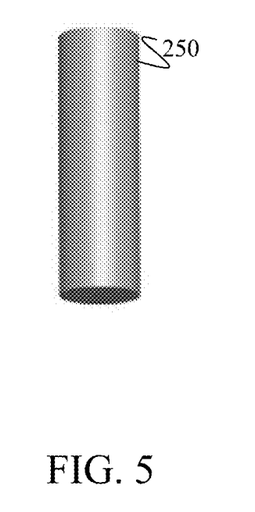
FIG. 5 is an isometric representation of a fiber filler for the embodiment of FIG. 4.
Figure 6:
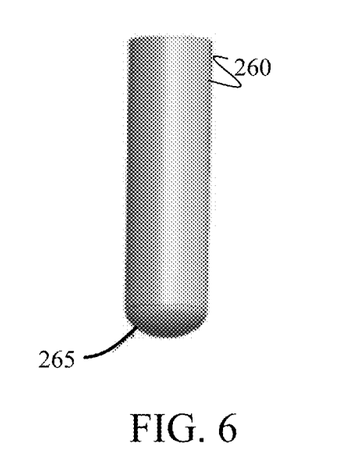
FIG. 6 is an isometric representation of a second embodiment of the fiber filler with a curved end.

The detail of an exemplary glass fiber 250 is shown in FIG. 5. The fiber 250 has flat ends 252. As a further alternative shown in FIG. 6, a fiber 260 is curved at the end 265 that is at the bond layer 235. The curvature at the end 265 of the fiber 260 promotes the distribution of the light exiting the fiber into the adhesive layer to penetrate further from the location of the glass fiber. It also aids the collection of the fluoresced light. The fiber end 265 is shown curved in FIG. 5, however other geometries are also possible, e.g., the fiber end could be faceted.

Figure 7:
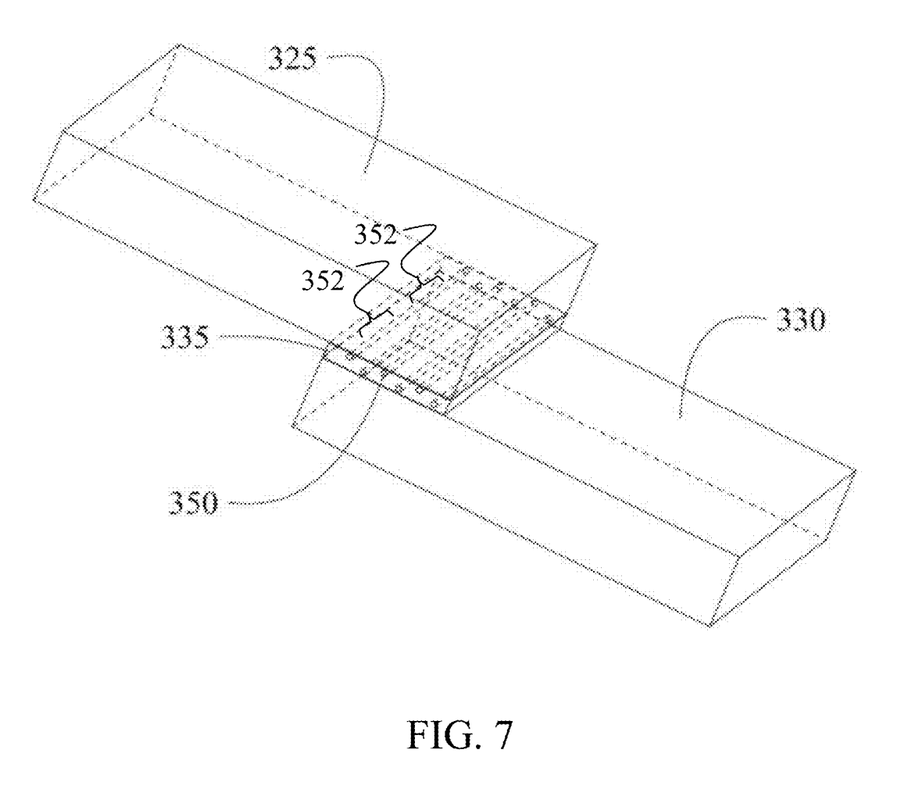
FIG. 7 is an isometric representation of a fourth embodiment of a composite bonded structure with integral stress sensing.
Figure 8:
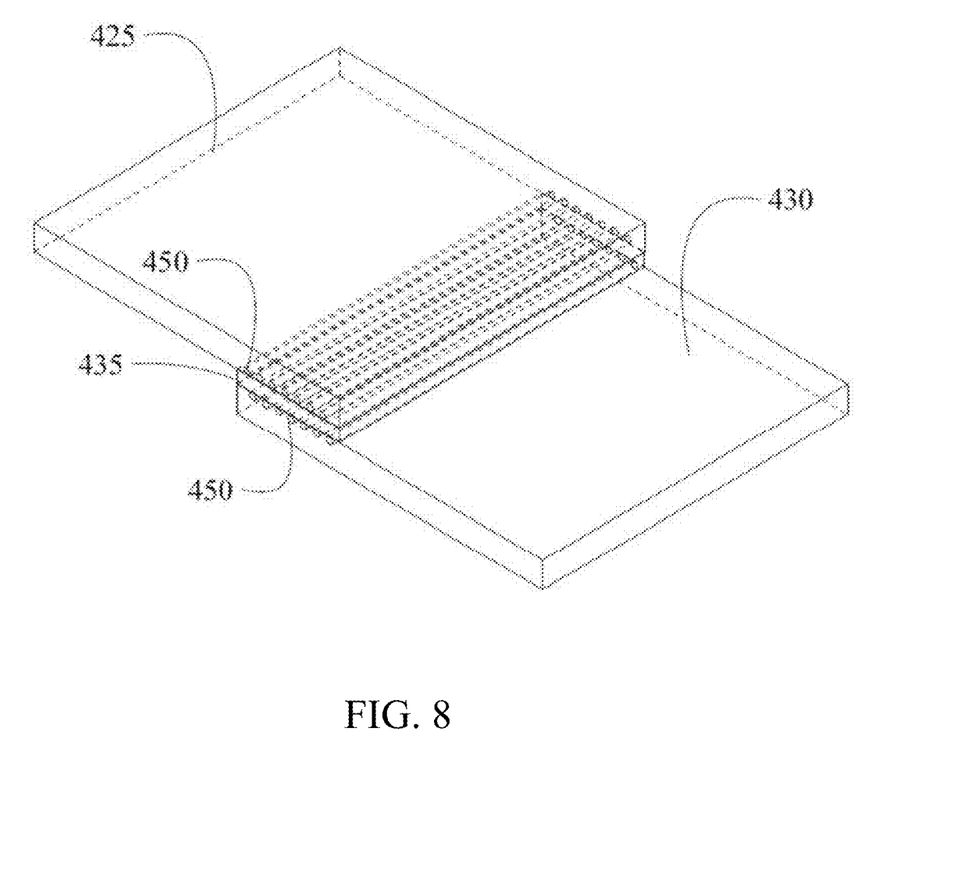
FIG. 8 is an isometric representation of a fifth embodiment of a composite bonded structure with integral stress sensing.

In the embodiments described above, the glass fibers are perpendicular to the thickness of the composite panels 225, 230. Alternatively, as shown in FIG. 7, glass fibers 350 may be inserted into the plane of the adhesive bond 335 (fiber diameter exaggerated for clarity). An advantage is that a single glass fiber can interrogate a larger area of bond. To enable this function the fibers needs to have outer surfaces modified for short distances 352 periodically along the length, so that the light that would ordinarily experience total internal reflection would find a surface in which exiting the fiber is possible. A further alternative embodiment to this approach is to place glass fibers 450 in the composite panel 425 and/or composite panel 430 on the surface that will be adjacent and parallel to the bond 435 as shown in FIG. 8 (fiber diameter exaggerated for clarity). Such fibers could be placed in the tow making the surface ply of the composite.

Figure 9:
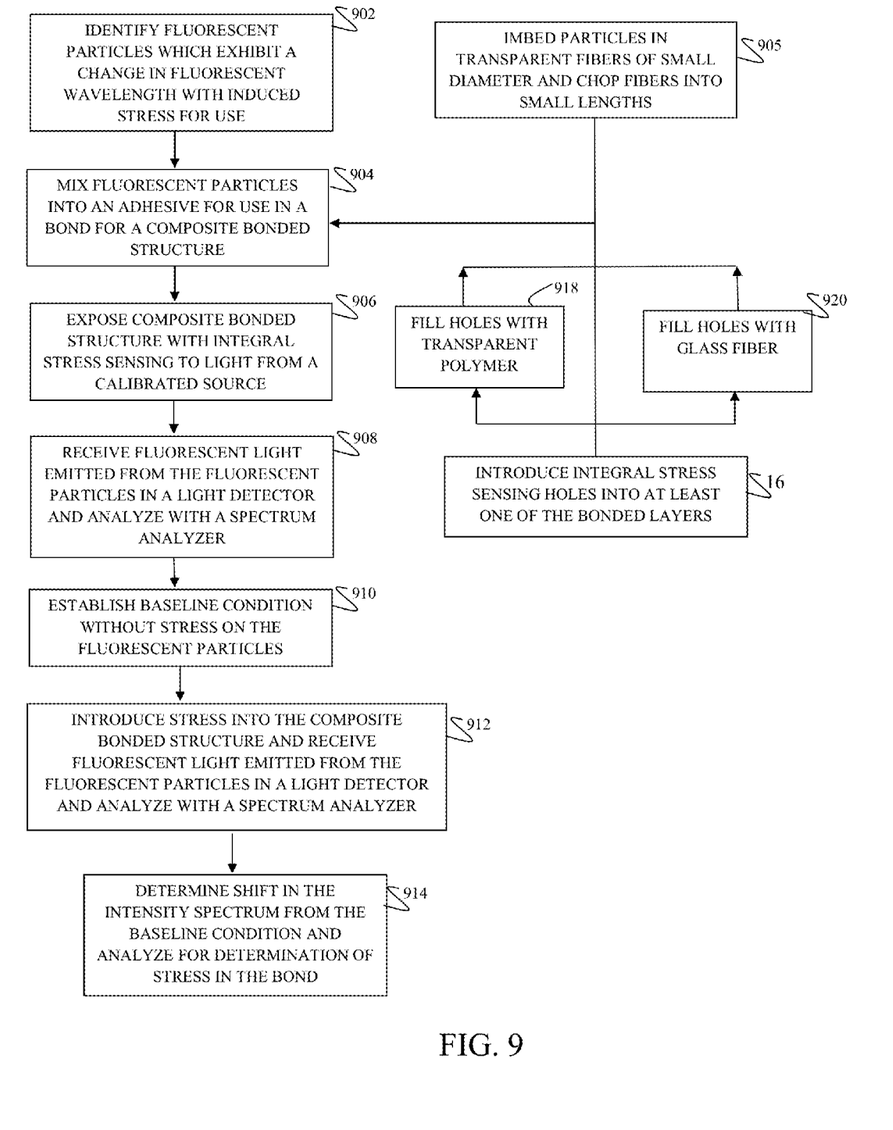
FIG. 9 is a flow chart of a stress sensing method using the embodiments described; and, FIG. 10 is a graph of an exemplary shift in spectral intensity.
Figure 10:
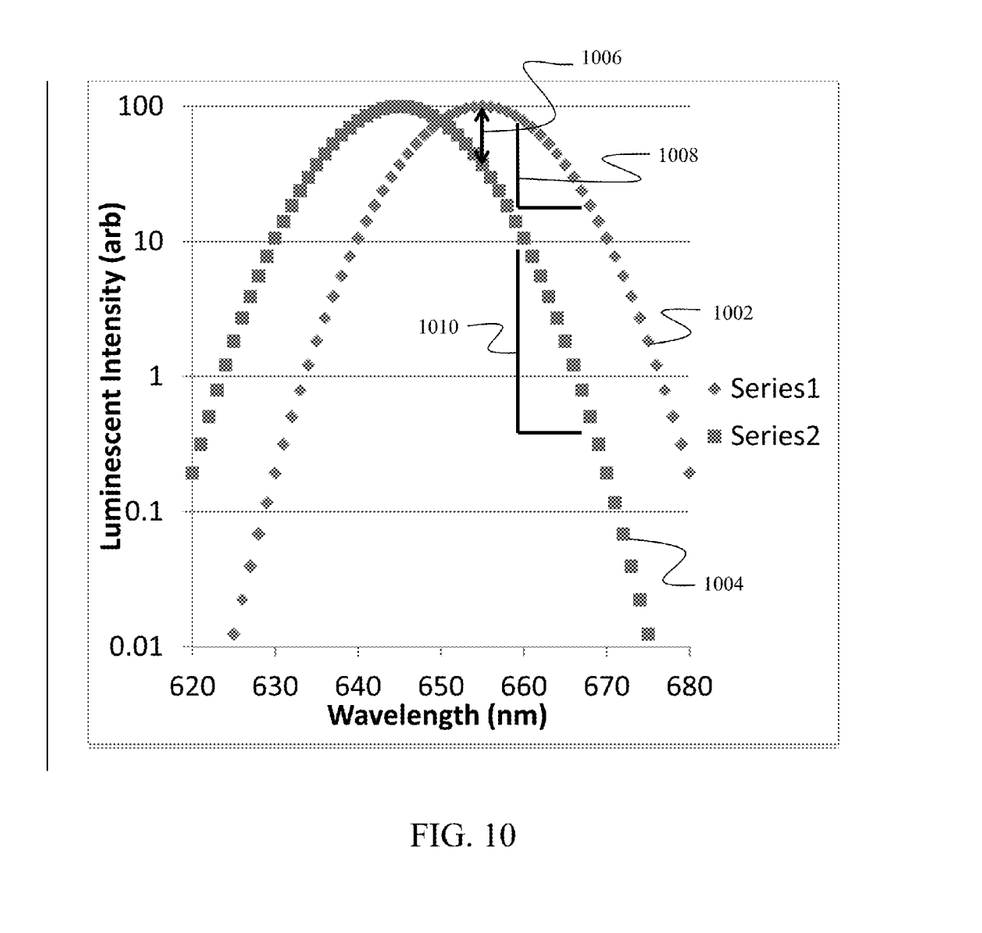

The embodiments for the composite bonded structure with integral stress sensing and bond evaluation system allows a method for determining stress in adhesive bond as shown in FIG. 9. Fluorescent particles which exhibit a change in fluorescent wavelength with induced stress are identified for use, step 902. The fluorescent particles are then mixed into an adhesive for use in a bond for a composite bonded structure with integral stress sensing, step 904. The fluorescent particles may be introduced directly into the adhesive or alternatively imbedded in transparent fibers of small diameter and the fibers chopped into small lengths which are then mixed into the adhesive, step 905. The composite bonded structure with integral stress sensing is then exposed to light from a calibrated source, step 906. Fluorescent light emitted from the fluorescent particles is then received in a light detector and analyzed with a spectrum analyzer, step 908. The light source may be a laser for highly coherent wavelength of the calibrated source. A baseline condition is established without stress on the fluorescent particles, step 910. Stress is then introduced into the composite bonded structure with integral stress sensing and fluorescent light emitted from the fluorescent particles in the stressed condition is then received in a light detector and analyzed with a spectrum analyzer, step 912. A determination of shift in the intensity spectrum from the baseline condition is then analyzed for determination of stress in the bond, step 914. An alternative to reporting the full spectral intensity is to measure the intensity at two discrete wavelengths and estimate the wavelength of peak intensity by the ratio of the two intensities at the discrete wavelengths. For example, two wavelengths, one on either of the leading or trailing edge of the wavelength of peak intensity could be chosen. The change in intensity at these wavelengths would be much larger than the change in intensity near the intensity maximum. An example is shown in FIG. 10, which shows luminescent intensity as a function of wavelength for two spectra, Series 1 1002 and Series 2 1004, with maxima at 645 nm and 655 nm, respectively. The spectra are calculated by assuming a Gaussian distribution and a halfwidth of 10 nm. In the measurement denoted as element 1006, the two spectra are distinguished by a measurement at 655 nm, in which Series 1 has an intensity of 100 and Series 2 would have an intensity of 36.8. The alternative measurement, illustrated by measurements denoted as elements 1008 and 1010, takes an intensity reading at 660 nm and 670 nm. In this method the ratio of the two, a value of 77.89/10.54=7.4 for Series 1, and a value of 10.54/0.193=54.6 for Series 2, provides a much larger difference than measuring at 655 nm.

Returning to FIG. 9, the light source and/or the detector may be scanned across the composite bonded structure with integral stress sensing to measure localized stress. To allow or enhance the incident light reception and/or fluorescing light emission, composite elements to be bonded in the composite bonded structure with integral stress sensing holes may be introduced into at least one of the bonded layers, step 916. The holes may be filled with transparent polymer, step 918, or glass fibers, step 920. The glass fibers may be inserted transverse to bond through at least one of the composite layers or parallel to the bond in surface roving layers of at least one of the composite layers. Alternatively, glass fibers may be introduced within the bond for transmission of the incident light and emitted fluorescent light.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. Process for bond stress measurement comprising:
identifying fluorescing particles sensitive to stress, said fluorescing particles emitting a first predetermined spectral intensity responsive to photons at a discrete wavelength in an unstressed condition and a second predetermined shifted spectral intensity responsive to photons at a discrete wavelength induced by a stressed condition;
mixing the fluorescing particles within an adhesive subsequently used in a bonded structure having a first fiber composite component, a second fiber composite component, a layer of the adhesive bonding the first fiber composite component and second fiber composite component;
providing a stimulus light with a light source emitting photons at the discrete wavelength for inducing fluorescence in the fluorescing particles;
observing characteristics of fluorescent light emitted from the fluorescing particles with a light detector receiving fluorescent light emitted from the fluorescing particles, said emitted light being indicative of the stress experienced by the fluorescing particles; and
translating the fluorescent light characteristics into stress data.

2. The process of claim 1 wherein fluorescing particles are first dispersed within small diameter transparent fiber, chopping the fiber into small lengths and mixing the fibers with the adhesive.

3. The process as defined in claim 1 wherein at least one of the two layers of material contains at least one hole allowing transmission of the stimulus light and fluorescent light emissions.

4. The process as defined in claim 3 wherein the hole is either open, filled with a transparent polymer, or filled with a glass fiber.

5. The process as defined in claim 1 wherein the step of translating the fluorescent light characteristics includes:
measuring the first predetermined spectral intensity of the fluorescent light with the fluorescing particles in an unstressed condition; and
measuring the second predetermined shifted spectral intensity of the fluorescent light with stress present in the bond.

6. The process as defined in claim 1 further wherein the step of observing the fluorescent light includes scanning the light source or the detector across the two layers of material and the bond to measure localized stress.

7. A composite bonded structure with integral stress sensing and bond evaluation system comprising:
a bonded structure having
a first fiber composite component;
a second fiber composite component;
a layer of adhesive bonding the first fiber composite component and second fiber composite component;
a plurality of fluorescing particles mixed in the adhesive to become embedded in the layer of adhesive, said fluorescing particles emitting a first predetermined spectral intensity responsive to photons at a discrete wavelength in an unstressed condition and a second predetermined shifted spectral intensity responsive to photons at the discrete wavelength induced by a stressed condition; and,
a bond evaluation apparatus for measuring spectral intensity, said bond evaluation apparatus having:
a light source emitting photons at the discrete wavelength for inducing fluorescence in the fluorescing particles;
a light detector receiving fluorescent light emitted from the fluorescing particles.

8. The composite bonded structure with integral stress sensing and bond evaluation system of claim 7 wherein the bond evaluation apparatus further comprises:

a spectrum analyzer measuring the spectral intensity of the fluorescent light, the spectral intensity proportional to stress in the adhesive bond.

9. The composite bonded structure with integral stress sensing and bond evaluation system of claim 8 wherein the light source is a laser.

10. The composite bonded structure with integral stress sensing and bond evaluation system of claim 9 wherein the light source or detector is scanned over the bonded structure.

11. The composite bonded structure with integral stress sensing and bond evaluation system of claim 7 wherein the fluorescing particles are quantum dots.

12. The composite bonded structure with integral stress sensing and bond evaluation system of claim 7 wherein the fluorescing particles are created from material selected from the set of cadmium selenide (CdSe), difluoroboron complex $BF_2AVB$ or crystals of $[(CH_3)_4N]_2MnCl_4$ or $[(CH_3)_4N]_2MnBr_4$.

13. The composite bonded structure with integral stress sensing and bond evaluation system of claim 7 wherein at least one of said first and second components is transparent to the light emitted from the light source and fluorescent light emitted from the fluorescing particles.

14. The composite bonded structure with integral stress sensing and bond evaluation system of claim 7 wherein at least one of said first and second components incorporates at least one hole extending through the component to the bond layer.

15. The composite bonded structure with integral stress sensing and bond evaluation system of claim 14 wherein the at least one hole is filled with transparent polymer.

16. The composite bonded structure with integral stress sensing and bond evaluation system of claim 14 wherein the at least one hole is filled with a glass fiber.

17. The composite bonded structure with integral stress sensing and bond evaluation system of claim 16 wherein the glass fiber has a curved end proximate the bond joint.

18. The composite bonded structure with integral stress sensing and bond evaluation system of claim 7 wherein at least one of said first and second components has at least one transparent fiber proximate and parallel to the bond joint.

19. The composite bonded structure with integral stress sensing and bond evaluation system of claim 7 further comprising at least one transmission fiber in the bond joint.

* * * * *